United States Patent [19]

Katsuragi et al.

[11] Patent Number: 5,407,921

[45] Date of Patent: Apr. 18, 1995

[54] METHOD FOR SUPPRESSING BITTER TASTE

[75] Inventors: Yoshihisa Katsuragi; Takeshi Yasumasu; Tomoshige Umeda; Susumu Yamasawa; Yuki Mitsui, all of Ibaraki, Japan

[73] Assignee: Kao Corporation, Tokyo, Japan

[21] Appl. No.: 269,034

[22] Filed: Jun. 30, 1994

[30] Foreign Application Priority Data

Jul. 1, 1993 [JP] Japan .................................. 5-163559

[51] Int. Cl.[6] ...................... A61K 31/66; A61K 31/685

[52] U.S. Cl. .......................................... 514/75; 514/76; 514/77; 514/78; 514/922; 424/49; 424/50; 424/51; 424/52; 424/53; 424/54; 424/55; 424/56; 424/57; 424/58

[58] Field of Search ....................... 514/75, 76, 77, 78, 514/922; 424/49, 50, 51, 52, 53, 54, 55, 56, 57, 58

*Primary Examiner*—Douglas W. Robinson
*Assistant Examiner*—Jean C. Witz
*Attorney, Agent, or Firm*—MaAulay Fisher Nissen Goldberg & Kiel

[57] ABSTRACT

A method for suppressing a bitter taste of material to be placed in mouth or in contact with mouth, such as foods, drinks, pharmaceuticals, comprises adding an acidic phospholipid or an acidic lysophospholipid to the material.

11 Claims, 1 Drawing Sheet

METHOD FOR SUPPRESSING BITTER TASTE

FIELD OF THE INVENTION

This invention relates to a method for suppressing a bitter taste of material to be placed in mouth or in contact with mouth, such as foods, drinks, pharmaceuticals for oral administration, and toiletries.

BACKGROUND OF THE INVENTION

A great number of foods, drinks, pharmaceuticals for oral administration, toiletries which have a bitter taste are known. Particularly, most of pharmaceuticals have a bitter taste, and some difficulty or pain arises when such pharmaceuticals are orally administered. Accordingly, suppression of a bitter taste of pharmaceuticals have been problems to be solved. Until now, the following methods have been known. Typically, addition of a sweetener or flavor has been employed. Japanese Patent Provisional Publication No. 2-56416 discloses addition of aspartame to pharmaceuticals, Also known are microcapsulation and coating using material soluble in stomach. Further known is chemical modification of a pharmaceutically active component. Japanese Patent Provisional Publication discloses use of a clathrate compound. These methods are employable only for specific compounds or the suppression of a bitter taste accomplished by these method appears insufficient.

For the suppression of a bitter taste in pharmaceuticals, the addition of a lipid is also known. For instance, Japanese Patent Publication No. 55-8966 discloses addition of lecithin (phosphatidylcholine) and cephalin singly or in combination. Japanese Patent Provisional Publication No. 62-265234 discloses addition of lecithin (phosphatidylcholine). These methods, however, are still insufficient to give the desired suppression of a bitter taste.

Infants and aged persons sometimes reject oral administration of solid pharmaceutical preparations. For this reason, syrup preparations are frequently employed. However, no appropriate methods to suppress a bitter taste of syrup preparations have been known.

In foods and drinks, there are certain bitter substances. For instance, bitter tastes of amino acids prepared by decomposition of proteins, bitter tastes of peptides, bitter taste of fruit or vegetable juices, and bitter tastes originating from flavor are mentioned. The presence of such bitter substances in foods and drinks sometimes lower quality of these foods and drinks. Removal of bitter tastes from foods and drinks have been reported as follows. Japanese Patent Provisional Publication No. 55-108254 proposes the use of an absorbent material, Japanese Patent Provisional Publication No. 61-40260 proposes the use of a clathrate confound, and Japanese Patent Provisional Publication describes addition of a sweetener. These methods, however, sometimes inappropriate, because the suppression of a bitter taste is not enough, or the addition of such compound alters taste of foods or drinks.

The problems of a bitter taste also resides in toiletries for the use on face and in mouth, such as lotions, mouthwashes and tooth pastes. For instance, surface active agents or flavors sometimes give bitter tastes. Therefore, the addition amount of surface active agents or flavors is sometimes limited. Until now, such bitter tastes have been masked by the use of sweeteners or specific flavors. However, such methods are not effective, if greatly bitter substances are involved.

SUMMARY OF THE INVENTION

The present invention has an object to provide a method for effectively and safely suppressing a bitter taste of foods, drinks, pharmaceuticals, toiletries, and the like. Particularly, the invention provides a method for safely suppressing bitter tastes of foods and drinks, without altering their favorite tastes.

It has been known that bitter substances (i.e., substances showing a bitter taste) have a hydrophobic group and that the bitter taste is sensed when the bitter substance is adsorbed by taste sensory cells of tongue at sites between lipid molecule and adjoining lipid molecule or between lipid molecule and adjoining protein molecule though the hydrophobic group. A strongly bitter substance shows high affinity to lipids. This mechanism has been confirmed by the study using a liposome composed of phospholipids. In more detail, when a bitter substance is added to liposomes to which a fluorescent dye is attached, the bitter substance is adsorbed by the liposome membrane, and the fluorescent dye is released. The amount of the released fluorescent dye increases when a strongly bitter substance is added. This means that bitter substances are easily adsorbed by phospholipids.

It has been now discovered by the inventors that an acidic phospholipid and an acidic lysophospholipid are effective to suppress bitter tastes of material.

Accordingly, the present invention resides in a method for suppressing a bitter taste of material to be placed in mouth or in contact with mouth, which comprises adding an acidic phospholipid or an acidic lysophospholipid to the material.

The acidic phospholipid or lysophospholipid is added, preferably in an amount of 0.01 to 60 weight parts (more preferably 0.05 to 30 weight parts) to one weight part of the material.

In the invention, the acidic phospholipid or lysophospholipid can be added to the material in the form of a lipid mixture containing at least 20 wt. % of the acidic phospholipid or lysophospholipid therein. Further, the acidic phospholipid or lysophospholipid can be preferably added to the material in the form of a lipid mixture whose neutral lipid content is less than 30 wt. %, more preferably less than 20 wt. %.

The acidic phospholipid or lysophospholipid can be preferably added to the material in the form of a lipid mixture whose neutral phospholipid content is 2 weight parts or less, preferably 0.2 weight part or less, per one weight part of the acidic phospholipid or lysophospholipid.

The acidic phospholipid or lysophospholipid can be coated on the surface of the material.

DETAILED DESCRIPTION OF THE INVENTION

Figure 1:
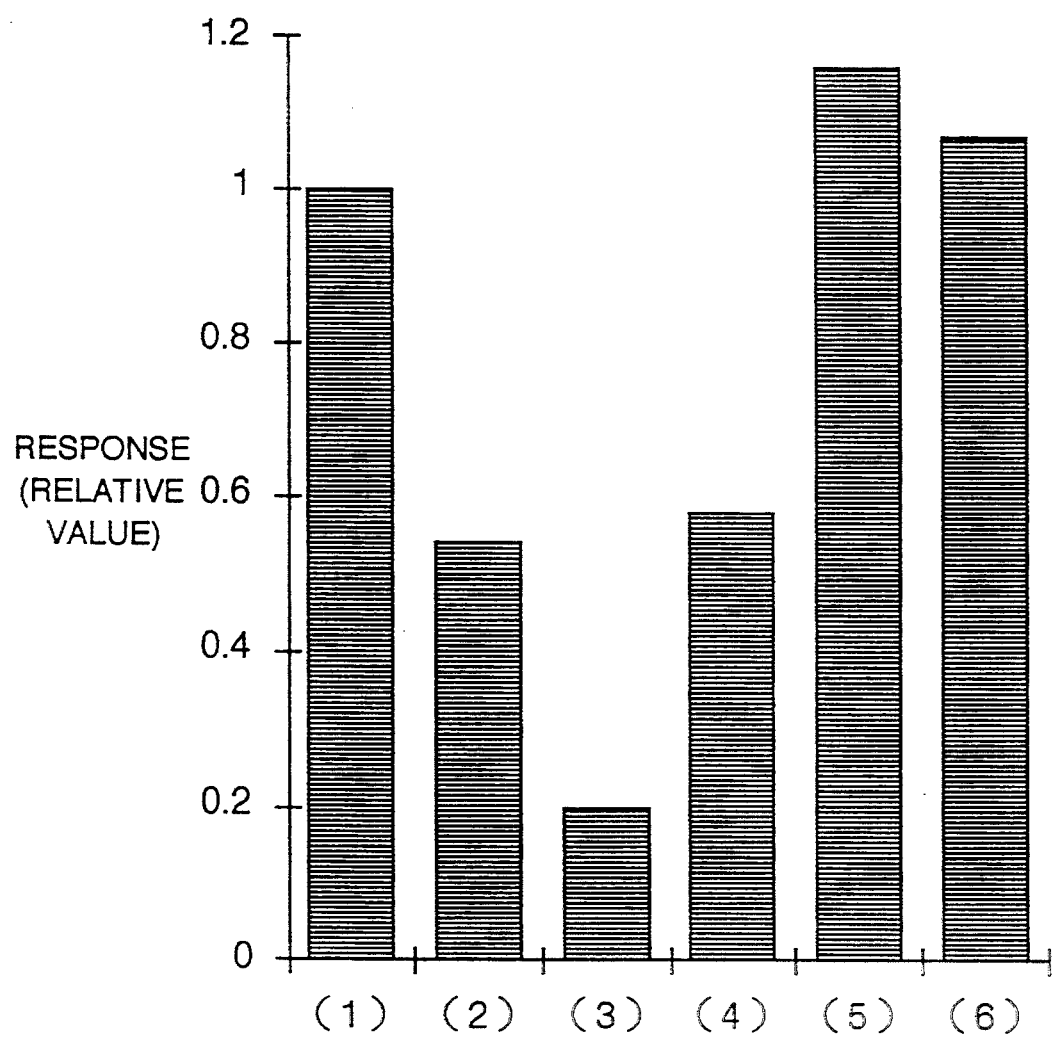
FIG. 1 shows experimental data which are obtained by the test using tongue of frog and indicate degree of suppression of bitter taste. (1) is for control. (2) to (4) are for the present invention, while (5) and (6) are for comparison.

In the invention, the acidic phospholipid or the acidic lysophospholipid is employed for suppressing bitter tastes of foods, drinks, pharmaceuticals, and the like.

The acidic phospholipid and acidic lysophospholipid means a phospholipid and a lysophospholipid, respectively, which show a negative charge in a physiologic saline solution at pH 7.0. Examples of the acidic phospholipids include phosphatidylserine, phosphatidic acid, phosphatidylglycerol (i.e., diphosphatidylglycerol). Examples of the acidic lysophospholipids include lysophosphatidylserine, lysophosphatidic acid, lysophosphatidylinositol, and lysophosphatidylglycerol.

The above acidic phospholipids and lysophospholipids can be obtained from soybean, the yellow of egg, an embryo bud of wheat, organs of animals, and various plant tissues by means of extraction or separation. The extraction can be performed using organic solvents having different polarity. The separation can be done by a process comprising adsorption on a silica gel column and elution with an organic solvent. The acidic phospholipids and lysophospholipids can be also obtained from other phospholipids by chemical modification and/or enzyme treatment. For instance, phosphatidic acid can be obtained by hydrolyzing phosphatidylcholine(neutral lipid) using phospholipase D which is obtained from oil-containing seeds (Japanese Patent Provisional Publication No. 2-312552), plants such as cabbage and rice bran, or microorganisms (Japanese Patent Provisional Publication No. 2-312551). Phosphatidylcholine can be converted into phosphatidylglycerol (Japanese Patent Provisional Publication No. 3-22991) and phosphatidylserine using the phospholipase D and performing ester-exchange of the phosphoryl group.

The acidic phospholipid and lysophospholipid can be obtained by chemical synthesis, such as phosphoric acid-esterification of diglyceride, phosphoric acid-esterification of monoglyceride, or fatty acid-esterification of glycerophosphoric acid. Examples of the synthetically obtainable acidic phospholipids and lysophospholipids include monoacylglycerol monophosphate, monoacylglycerol diphosphate, bisphosphatidic acid, bisphosphatidyl-monophosphatidic acid, and bisphosphatidyl-lysophosphatidic acid. Further, hydrogenated acidic phospholipids and lysophospholipids can be also employed as the acidic phospholipids and lysophospholipids in the invention.

As described above, the acidic phospholipids and lysophospholipids of the invention can be of natural origin or can be obtained by synthetic process. Accordingly, the acidic phospholipid or lysophospholipid of the invention is generally employed in the form of a mixture containing other lipid components such as neutral phospholipids (e.g., phosphatidylcholine, phosphatidylethanolamine, and their lyso-derivatives), neutral lipids (e.g., triglycerides, diglycerides, monoglycerides), fatty acids, sterol-type lipids, and glycolipids. In that case, the acidic phospholipid or lysophospholipid of the invention is preferably contained in the mixture in an amount of not less than 20 weight %, more preferably not less than 60 weight %, and most preferably not less than 70 weight %.

As the acidic phospholipids and lysophospholipids of the invention, phosphatidic acid and lysophosphatidic acid are preferred, because these acids show specifically high bitter taste suppression. Most preferred is phosphatidic acid. The phosphatidic acid and/or lysophosphatidic acid is preferably contained in the above-mentioned lipid mixture in an amount of not less than 5 weight %, more preferably not less than 20 weight %, and most preferred not less than 50 weight %.

According to the study by the inventors, the bitter taste suppression activity of the acidic phospholipid and lysophospholipid increases under the condition that neutral lipids are not co-existing. Accordingly, the content of neutral lipids in the lipid mixture is preferably lowered, for instance, not more than 30 weight %, more preferably not more than 25 weight %, and most preferably not more than 20 weight %. Further, the co-existence of neutral phospholipids in the lipid mixture is also disadvantageous. Therefore, the neutral phospholipid content in the lipid mixture preferably is not more than 50 in the lipid mixture preferably is not more than 50 weight %, more preferably not Tare than 30 weight %, and most preferably not more than 10 weight %. From other aspects, the neutral phospholipid content preferably is less than twice as much as the total content of the acidic phospholipid and lysophopholipid. The neutral phospholipid content is more preferred to be less than one-twice ($\frac{1}{2}$), most preferred to be less than one-tenth (1/10), and especially preferred to be less than one-fifties (1/50), of the total content of the acidic phospholipid and lysophospholipid.

The increase of content of the acidic phospholipid and lysophospholipid and the decease of neutral lipid content in the lipid mixture can be accomplished, for instance, by enzymic decomposition and/or solvent fractionation, followed by acetone processing and/or membrane separation.

In the method of the invention, the acidic phospholipid or lysophospholipid can be added to foods, drinks, pharmaceuticals, and the like in the form of powder, granules, pellet, troche, paste, syrup, solution, or emulsion. The acidic phospholipid or lysophospholipid is generally added to the material having a bitter taste in the amount of not less than 0.001 weight part per one weight part of the material.

In the case that the material having a bitter taste is in the form of an aqueous solution, an aqueous suspension, or an emulsion, the acidic phospholipid or lysophospholipid can be added to one weight part of the solution, suspension, or emulsion in the amount of 0.01 to 60 weight parts, preferably in the amount of 0.05 to 30 weight parts, and more preferably 0.1 to 10 weight parts. In the case that the material having a bitter taste is in the form of a solid or paste, the acidic phospholipid or lysophospholipid can be added to one weight part of the solid or paste in the amount of 0.01 to 60 weight parts, more preferably in the amount of 0.5 to 20 weight parts.

The addition of the acidic phospholipid or lysophospholipid of the invention is further described below with reference to foods, drinks, pharmaceuticals, and toiletries, respectively.

Examples of foods having a bitter taste include citrus fruits such as grape fruit, orange, and lemon; vegetables such as tomato, pimento, celery, melon, carrot, potato, and asparagus; seasoning or flavoring materials such as flavor, sauces, soysauce, bean paste(miso), deliciousness-imparting materials, and red pepper; foods originating from soybean; emulsion foods such as cream, dressing, mayonnaise, and margarine; processed marine products such as fish meat, ground fish meat, and fish eggs; nuts such as peanuts; fermented foods such as fermented soybean; meats and processed meats; pickles; noodles; soups including powdery soups; dairy products such as cheese; breads and cakes; confectioneries such as candies, chewing gum, and chocolate; and specifically prepared foods for health. Further, the acidic phospholipid or lysophospholipid can be employed for suppressing bitter tastes of amino acids, peptides, and oligosaccharide, such as leucine, isoleucine, and phenylalanine.

Examples of the drinks having a bitter taste include juices of citrus fruits and vegetables; soybean milk, coffee, cocoa, black tea, green tea, fermented tea, semi-fermented tea, refreshing drinks, beverages, and milk.

The acidic phospholipid and lysophospholipid can be added to the food or drink in the amount of 0.05 to 30 weight %, preferably 0.1 to 20 weight %, more preferably 0.5 to 15 weight %, most preferably 1 to 10 weight % (specifically 1 to 5 weight %) per the total amount of the food or drink.

There are no specific limitations with respect to the orally administrable pharmaceuticals whose bitter tastes can be suppressed by addition of the acid phospholipid or lysophospholipid of the invention. Typical examples of the orally administrable pharmaceuticals are acid addition salts of basic pharmaceutically active components such as strychnine, quinine, papaverine, berberine, promethazine, brucine, propranolol, and chlorpromazine. In more detail, inorganic acid salts and organic acid salts such as hydrochloride, nitrate, sulfate, acetate, citrate, and carbonate of basic pharmaceutically active components can be mentioned.

The pharmaceuticals can be in any preparation forms such as solid preparations (e.g., capsule, granules, medicinal pill, powder, pellet, troche and dry syrup); and liquid preparations (e.g., liquids, extracts, elixirs, spirits, syrups, aromatic water, lemonades, and fluid-extracts).

The acidic phospholipid or lysophospholipid can be incorporated into the pharmaceutical preparation in any conventional manners. For instance, the acidic phospholipid or lysophospholipid can be incorporated into the pharmaceutical preparation singly or in combination with one or more of known additives. Examples of such known additives include diluent, filler, excipient, vehicle, binder, disintegrator, lubricant, fluidity-improving agent, coating agent, flavor, masking agent, perfume, and anti-oxidation agent. The pharmaceutical preparation can be produced using granulating machines such as planetary mixer, stirring granulator, high speed mixing granulator, extruding granulator, fluidized bed granulator, centrifugal rolling granulator, and roller compactor.

The acidic phospholipid and lysophospholipid can be incorporated to the pharmaceutical preparation in the amount of 0.01 to 60 weight %, preferably 0.05 to 50 weight %, more preferably 0.1 to 30 weight %, most preferably 0.5 to 20 weight % (specifically 1 to 10 weight %) per the total amount of the pharmaceutical preparation. From a different viewpoint, the acidic phospholipid and lysophospholipid can be added to one weight part of the pharmaceutically active component(s) in the amount of 0.01 to 1,000 weight parts (preferably 0.1 to 100 weight parts).

Examples of the toiletries showing a bitter taste include toiletries for face treatment, such as lotion, milky lotion, cream, pack, lipstick, foundation, shaving lotion, after-shaving lotion, cleansing foam, and cleansing gel, and agents for treatment of mouth, such as tooth paste, mouthwash, and mouthrinse. Examples of bitter substances employed for the incorporation into toiletries include surface active agents such as sodium alkylsulfate and sodium monoalkylphosphate; flavors such as menthol, linalol, phenylethyl alcohol, ethyl propionate, geraniol, linalol acetate, and benzyl acetate; bactericides such as methylparaben, propylparaben, and butylparaben; humecrants such as lactic acid and sodium lactate; alcohol denaturants such as 8-acetylated saccharose and brucine; and astringents such as aluminum lactate.

The acidic phospholipid and lysophospholipid can be incorporated to the toiletry in the amount of 0.05 to 30 weight %, preferably 0.1 to 20 weight %, more preferably 0.5 to 15 weight %, most preferably 1 to 10 weight % (specifically 1 to 5 weight %) per the total amount of the toiletry. From a different viewpoint, the acidic phospholipid and lysophospholipid can be added to one weight part of the substance having a bitter taste in the amount of 0.1 to 1,000 weight parts (preferably 1 to 100 weight parts).

The acidic phospholipid and lysophospholipid can be coated on a substance having a bitter taste. For instance, foods in the form of solid, such as candy, other confectioneries, processed fish meats, vegetables, fruits, processed vegetables, processed fruits, dried vegetable juices, and dried fruits juices and pharmaceutical preparations in the form of powder, granules, pellets, tablets, soft and hard capsules, and pills. The coating layer can comprise the acidic phospholipid or lysophospholipid and a hydrophilic polymer. Examples of the hydrophilic polymers include cellulose derivatives, gelatin, and polyvinyl alcohol. Other additives such as sweeteners and flavors can be incorporated into the coating layer. There is no need of coating the whole surface of the material. Partial coating is also employed.

The coating amount of the acidic phospholipid or lysophospholipid can be 0.05 to 30 weight % (preferably 0.1 to 20 weight %, more preferably 1 to 10 weight %) based on the total amount of the material to be coated, if the material is one of foods, and can be 0.01 to 60 weight % (preferably 0.1 to 30 weight %, more preferably 1 to 10 weight %) based on the total amount of the material to be coated, if the material is a pharmaceutical.

The coating with the acidic phospholipid or lysophospholipid can be made on the material which already contains the acid phospholipid or lysophospholipid.

For the coating, any known coating methods and coating apparatuses can be used.

The present invention is further described in more detail by the following examples. In the examples, "part(s)" and "%" mean "weight part(s)" and "%", respectively.

PREPARATION OF LIPID SAMPLES (1) Preparation of Lipid Sample 1

20 g of defatted lecithin purchased from market (SLPW-SP, produced by True Lecithin Industries Co., Ltd.) was placed in a four-necked 500-mL volume flask equipped with stirrer. To the lecithin were added 125 mL of 0.1M Tris hydrochloric acid buffer (pH 6–8) and 340 mL of hexane/ethyl acetate (2/1, v/v). They were mixed under stirring. To the mixture were added 150 mL of aqueous calcium hydrochloride (1M) and 150 mL of an aqueous solution of 15 units of phospholipase D of microorganism origin (origin: *Streptomyces chromofuscus*, produced by Asahi Chemical Industries, Co., Ltd.). The resulting mixture was stirred at 30° C. for 14 hrs. The reaction mixture was then allowed to stand for separation of a solvent portion. The solvent portion was placed under reduced pressure to distill off the solvent. The residue was analyzed for determination of its lipid composition on a thin layer silica gel plate (Kieselgel, produced by Merk & Co., Inc.) and by observing color development with sulfuric acid. The results are set forth in Table 1.

(2) Preparation of Lipid Sample 2

150 g of phosphatidylcholine purchased from market (Epichlor S 200, produced by Lucas Mayer Co.) was placed in a four-necked 5,000-mL volume flask equipped with stirrer. To the phosphatidylcholine was added 1,500 mL of hexane/ethyl acetate (2/1, v/v). They were mixed under stirring to give a solution. To the solution were added 1,500 mL of aqueous acetate buffer(pH 8) of 100 units of the phospholipase D of microorganism origin, and then 100 g of calcium chloride. The resulting mixture was stirred at 37° C. for 36 hrs. The reaction mixture was then allowed to stand for separation of a solvent portion. The solvent portion was placed under reduced pressure to distill off the solvent. The residue (yield: approx. 100 g) was analyzed for determination of its lipid composition on a thin layer silica gel plate (Kieselgel) and by observing color development with sulfuric acid. The results are set forth in Table 1.

(3) Preparation of Lipid Sample 3

25 g of silky bean (produced in U.S.A.) was mixed with 150 g of 1M acetate buffer(pH 6). The resulting mixture was pulverized under wet condition at room temperature and centrifuged for 10 min. at 3,000 r.p.m., to give 120 g of a supernatant (extract).

25 g of the defatted lecithin purchased from market (SLPW-SP) was placed in a four-necked 500-mL volume flask equipped with stirrer. To the lecithin was added 120 g of the above-obtained extract. To the mixture under stirring were successively added 250 ml of ethyl acetate and 32.5 g of water. The mixture was stirred at 30° C. for 20 hrs. The reaction mixture was then allowed to stand for separating an ethyl acetate portion from an aqueous portion. The ethyl acetate portion was placed under reduced pressure to give a residue. The aqueous portion was extracted with two portions of chloroform/methanol (2/1, v/v). The obtained extract was subjected to Folch method for partitioning. The partitioned solution was combined with the residue separated from the ethyl acetate portion, and placed under reduced pressure to distill off chloroform and methanol. There was obtained 22 g of a lipid mixture as residue. The residue was analyzed for determination of its lipid composition on a thin layer silica gel plate (Kieselgel) and by observing color development with sulfuric acid. The results are set forth in Table 1.

TABLE 1

| Lipid Composition | Lipid Sample 1 | Lipid Sample 2 | Lipid Sample 3 |
|---|---|---|---|
| Neutral Phospholipid | | | |
| PC | 0% | 0% | 0% |
| PE | 0 | 0 | 0 |
| Acidic Phospholipid | | | |
| PI | 7.8 | 0 | 0 |
| PA | 54.2 | 94.0 | 62.0 |
| PS | 0.1 | 0 | 0.1 |
| L-PA | 0.5 | 1.0 | 0.9 |
| Neutral Lipid | 18.4 | 4.0 | 18.0 |

TABLE 1-continued

| Lipid Composition | Lipid Sample 1 | Lipid Sample 2 | Lipid Sample 3 |
|---|---|---|---|
| Glycolipid | 19.0 | 1.0 | 19.0 |

Remarks:
PC: phosphatidylcholrine,
PE: phosphatidylethanolamine,
PI: phosphatidylinositol,
PA: phosphatidic acid,
PS: phosphatidylserine,
L-PA: lysophosphatidic acid

EXAMPLE 1

Test Samples: Grape Fruit Juice, Orange Juice, and Vegetable Juice

To the juice was added Lipid Sample 2 to give a juice sample containing the lipid sample at a concentration of 0.1% or 0.3%. The juice sample was well mixed.

The juice sample was subjected to sensory evaluation by a panel of ten members (age: twenties to forties) with respect to bitter taste. The evaluation was performed by classifying bitter tastes into the following five classes:

Level 5: Strong bitter taste is sensed.
Level 4: Bitter taste is not strong, but clearly sensed.
Level 3: Some bitter taste is sensed.
Level 2: Slightly bitter taste is sensed.
Level 1: No bitter taste is sensed.

Further, a juice with no addition of lipid sample was prepared as control.

The results are set forth in Table 2.

TABLE 2

| Juice Sample | Bitterness Level(average) |
|---|---|
| Grape fruit juice (control) | 4.2 |
| Grape fruit juice plus 0.1% Lipid Sample 2 | 2.2 |
| Grape fruit juice plus 0.3% Lipid Sample 2 | 1.3 |
| Orange juice (control) | 3.8 |
| Orange juice plus 0.1% Lipid Sample 2 | 1.8 |
| Orange juice plus 0.3% Lipid Sample 2 | 1.0 |
| Vegetable juice (control) | 4.2 |
| Vegetable juice plus 0.1% Lipid Sample 2 | 2.8 |
| Vegetable juice plus 0.3% Lipid Sample 2 | 2.0 |

It is apparent that the addition of Lipid Sample 2 according to the invention suppresses bitter tastes of fruit and vegetable juices.

EXAMPLE 2

Test Samples: Instant Coffee, and Regular Coffee

To the coffee was added Lipid Sample 3 to give a coffee sample containing the lipid sample at a concentration of 0.1% or 0.3%. The coffee sample was well mixed.

The coffee sample was then evaluated in the same manner as that described in Example 1. A coffee with no addition of lipid sample was also prepared as control.

The results are set forth in Table 3.

TABLE 3

| Coffee Sample | Bitterness Level(average) |
|---|---|
| Instant coffee (control) | 4.3 |
| Instant coffee plus 0.1% Lipid Sample 3 | 1.8 |
| Instant coffee plus 0.3% Lipid Sample 3 | 1.3 |
| Regular coffee (control) | 4.8 |
| Regular coffee plus 0.1% Lipid Sample 3 | 2.2 |
| Regular coffee plus 0.3% Lipid Sample 3 | 1.0 |

It is apparent that the addition of Lipid Sample 3 according to the invention suppresses bitter tastes of various coffees. Thus, coffees giving a milder taste can be prepared.

EXAMPLE 3

Test Sample: Powdery Soup

To the powdery soup was added Lipid Sample 1 to give a soup sample containing the lipid sample at a concentration of 0.1% or 0.3%. The soup sample was well mixed.

The soup sample was then evaluated in the same manner as that described in Example 1. A soup with no addition of lipid sample was also prepared as control.

As a result, suppression of a bitter taste of a soup prepared using a powdery soup by the lipid sample was confirmed.

EXAMPLE 4

Test Sample: Propranolol (Pharmacologically Active Component Showing a Strong Bitter Taste)

To an aqueous solution of prepranol (10 mM) was added Lipid Sample 2 to give an aqueous prepranol sample containing the lipid sample at a concentration of 0.3% (w/v) or 1.0% (w/v). The propranolol sample was well mixed.

The aqueous propranolol sample was then evaluated in the below-mentioned manner. An aqueous prepranol solution (10 mM) containing 15% (w/v) of sucrose or sorbitol in place of the lipid sample was also prepared as control.

The aqueous propranolol sample was subjected to sensory evaluation by a panel of ten to fifteen members having normal sense of taste with respect to bitter taste. The evaluation was performed by the following equivalent concentration test.

Equivalent Concentration Test

Ten reference solutions of quinine sulfate having ten different levels of bitter taste in which differences of bitterness between two adjoining levels are adjusted to be equivalent to each other are prepared. The aqueous propranolol sample and the reference solutions are compared with each other by the panel for determining the bitter taste of the propranolol sample by the corresponding reference solution. The strength of sense of a taste is proportional exponentially to the concentration of the substance having the taste. Accordingly, the differences of concentration between two adjoining levels differs from each other. However, the differences of bitterness between all two adjoining levels are the same.

| Level of Bitterness | Concentration of Quinine Sulfate | Level of Bitterness | Concentration of Quinine Sulfate |
| --- | --- | --- | --- |
| 1 | 0.00022 g/100 ml | 6 | 0.0037 g/100 ml |
| 2 | 0.00048 | 7 | 0.0058 |
| 3 | 0.0009 | 8 | 0.0094 |
| 4 | 0.0015 | 9 | 0.015 |
| 5 | 0.0023 | 10 | 0.0245 |

The results are set forth in Table 4.

TABLE 4

| Aqueous Propranolol Sample | Bitterness Level(average) |
| --- | --- |
| Aqueous propranolol (control) | 9.4 |

TABLE 4-continued

| Aqueous Propranolol Sample | Bitterness Level(average) |
| --- | --- |
| Aqueous propranolol plus 0.3% Lipid Sample 2 | 5.6 |
| Aqueous propranolol plus 1.0% Lipid Sample 2 | 4.3 |
| Aqueous propranolol plus 15.0% sucrose | 6.9 |
| Aqueous propranolol plus 15.0% sorbitol | 7.8 |

It is apparent that the addition of Lipid Sample 2 according to the invention suppresses a bitter taste of propranolol. Accordingly, an aqueous propranolol preparation which is easily administered orally can be prepared.

EXAMPLE 5

Test Samples: Quinine, Promethazine, Papaverine, Chloropromazine, Berberine, Brucine, Strychnine To an aqueous solution of the test sample(10 mM) was added Lipid Sample 2 to give an aqueous sample containing the lipid sample at a concentration of 0.3% (w/v) or 1.0% (w/v). An aqueous solution of the test sample with no addition of lipid sample was also prepared as control. The quinine was employed in its hydrochloride as usual. In the following examples, the quinine was also used in its hydrochloride.

As a result, suppression of a bitter taste of a test sample by the lipid sample was confirmed. Accordingly, an aqueous pharmaceutical preparation which is easily administered orally can be prepared.

EXAMPLE 6

Test Sample: Quinine Hydrochloride

A granular preparation was prepared by extruding the following composition.

| | |
| --- | --- |
| Quinine hydrochloride (active component) | 1 part |
| Gelatinized starch | 7 parts |
| Corn starch | 32 parts |
| Lactose | 55 parts |
| Lipid sample 3 | 5 parts |

A control granular preparation was also prepared in the same manner except that no lipid sample was incorporated and the amount of lactose was changed to 60 parts. A comparative granular preparation was further prepared in the same manner except that the lipid sample 3 was replaced with the same amount of lecithin (i.e., phosphatidylcholine).

The granular preparation sample was subjected to sensory evaluation by the equivalent concentration test. The results are set forth in Table 5.

TABLE 5

| Granular preparation of quinine hydrochloride | Bitterness Level(average) |
| --- | --- |
| Granular preparation(control) | 8.4 |
| Granular preparation plus Lipid Sample 3 | 4.5 |
| Granular preparation plus lecithin(comparative) | 7.8 |

It is apparent that the addition of Lipid Sample 3 according to the invention suppresses bitter taste of quinine hydrochloride. Accordingly, a granular quinine preparation which is easily administered orally can be prepared.

EXAMPLE 7

Test Samples: Quinine, Promethazine, Papaverine, Chloropromazine, Berberine, Brucine, Strychnine A granular preparation was prepared in the same manner as in Example 6, using the above-mentioned test sample. A granular preparation of the test sample with no addition of lipid sample was also prepared as control.

As a result, suppression of a bitter taste of a test sample by the lipid sample was confirmed. Accordingly, a granular pharmaceutical preparation which is easily administered orally can be prepared.

EXAMPLE 8

Test Sample: Quinine Hydrochloride

A granular preparation was prepared by extruding the following composition.

| Quinine hydrochloride (active component) | 10 parts |
|---|---|
| Gelatinized starch | 10 parts |
| Corn starch | 25 parts |
| Lactose | 35 parts |
| Lipid sample 2 | 20 parts |

A control granular preparation was also prepared in the same manner except that no lipid sample was incorporated and the amount of lactose was changed to 55 parts. A comparative granular preparation was further prepared in the same manner except that the lipid sample 2 was replaced with the same amount of lecithin (i.e., phosphatidylcholine).

The granular preparation sample was subjected to sensory evaluation by the equivalent concentration test.

The results are set forth in Table 6.

TABLE 6

| Granular preparation of quinine hydrochloride | Bitterness Level(average) |
|---|---|
| Granular preparation(control) | 9.9 |
| Granular preparation plus Lipid Sample 2 | 5.5 |
| Granular preparation plus lecithin(comparative) | 9.7 |

It is apparent that the addition of Lipid Sample 2 according to the invention suppresses bitter taste of quinine hydrochloride. Accordingly, a granular quinine preparation which is easily administered orally can be prepared.

EXAMPLE 9

Test Samples: Quinine, Promethazine, Papaverine, Chloropromazine, Berberine, Brucine, Strychnine A granular preparation was prepared in the same manner as in Example 8, using the above-mentioned test sample. A granular preparation of the test sample with no addition of lipid sample was also prepared as control.

As a result, suppression of a bitter taste of a test sample by the lipid sample was confirmed. Accordingly, a granular pharmaceutical preparation which is easily administered orally can be prepared.

EXAMPLE 10

Test Samples: Quinine, Promethazine, Papaverine, Chloropromazine, Berberine, Brucine, Strychnine A pellet was prepared in the conventional manner using the preparation composition described in one of Examples 6, 7, 8 and 9. A pellet of the test sample with no addition of lipid sample was also prepared as control.

As a result, suppression of a bitter taste of a test sample by the lipid sample was also confirmed.

EXAMPLE 11

Test Sample: Quinine Hydrochloride

A granular preparation was prepared by the rolling granulation process using the following composition.

| Quinine hydrochloride (active component) | 1 part |
|---|---|
| Corn starch | 35 parts |
| Mannitol | 58 parts |
| Hydroxypropylcellulose(content: 15%) | 3.5 parts |
| Lipid sample 2 | 1 part |

A control granular preparation was also prepared in the same manner except that no lipid sample was incorporated and the amount of marmitol was changed to 59 parts. A comparative granular preparation was further prepared in the same manner except that the lipid sample 2 was replaced with the same amount of lecithin (i.e., phosphatidylcholine).

The granular preparation sample was subjected to sensory evaluation by the equivalent concentration test.

The results are set forth in Table 7.

TABLE 7

| Granular preparation of quinine hydrochloride | Bitterness Level(average) |
|---|---|
| Granular preparation(control) | 8.1 |
| Granular preparation plus Lipid Sample 2 | 4.8 |
| Granular preparation plus lecithin(comparative) | 7.5 |

It is apparent that the addition of Lipid Sample 2 according to the invention suppresses bitter taste of quinine hydrochloride. Accordingly, a granular quinine preparation which is easily administered orally can be prepared.

EXAMPLE 12

Test Sample: Quinine Hydrochloride

A granular preparation was prepared by the rolling granulation process using the following composition.

| Quinine hydrochloride (active component) | 10 parts |
|---|---|
| Corn starch | 25 parts |
| Mannitol | 50 parts |
| Hydroxypropylcellulose(content: 15%) | 5 parts |
| Lipid sample 3 | 1 part |

A control granular preparation was also prepared in the same manner except that no lipid sample was incorporated and the amount of lactose was changed to 60 parts. A comparative granular preparation was further prepared in the same manner except that the lipid sample 3 was replaced with the same amount of lecithin (i.e., phosphatidylcholine).

The granular preparation sample was subjected to sensory evaluation by the equivalent concentration test.

The results are set forth in Table 8.

TABLE 8

| Granular preparation of quinine hydrochloride | Bitterness Level(average) |
|---|---|
| Granular preparation(control) | 9.5 |
| Granular preparation plus Lipid Sample 3 | 5.6 |

TABLE 8-continued

| Granular preparation of quinine hydrochloride | Bitterness Level(average) |
|---|---|
| Granular preparation plus lecithin(comparative) | 9.2 |

It is apparent that the addition of Lipid Sample 3 according to the invention suppresses bitter taste of quinine hydrochloride. Accordingly, a granular quinine preparation which is easily administered orally can be prepared.

EXAMPLE 13

Test Sample: Promethazine

In 100 mL of purified water, 40 mg of butyl p-oxybenzoate was heated to give an aqueous solution. To the solution was added 150 g of refined white sugar, and the mixture was stirred to give a homogenous solution. To the cooled solution was then added promethazine to give a solution of 5 mM concentration, and the mixture was stirred to give a homogenous solution. To the mixture was further added Lipid Sample 1 to give a solution containing 1.0% lipid sample. After the mixture was stirred, purified water was added to make a diluted solution of 360 mL. Thus, a syrup preparation was prepared. A syrup preparation of the test sample with no addition of lipid sample was also prepared as control. Also prepared was a syrup preparation in which Lipid Sample 1 was replaced with lecithin (i.e., phosphatidylcholine).

The syrup preparation sample was subjected to sensory evaluation by the equivalent concentration test.

The results are set forth in Table 9.

TABLE 9

| syrup preparation of promethazine | Bitterness Level(average) |
|---|---|
| Syrup preparation(control) | 7.9 |
| Syrup preparation plus Lipid Sample 1 | 3.8 |
| Syrup preparation plus lecithin(comparative) | 6.9 |

It is apparent that the addition of Lipid Sample 1 according to the invention suppresses bitter taste of promethazine in syrup. Accordingly, a promethazine syrup which is easily administered orally can be prepared.

EXAMPLE 14

Test Sample: Quinine Hydrochloride

A coated granular preparation was prepared from the following compositions I and II by the following rolling granulation process.

| Composition I | |
|---|---|
| Quinine hydrochloride (active component) | 1 part |
| Corn starch | 35 parts |
| Lactose | 54.5 parts |
| Hydroxypropylcellulose(content: 15%) | 3.5 parts |
| Composition II | |
| Lipid sample 1 | 1 part |
| Hydroxypropylcellulose(content: 15%) | 5 parts |

Rolling Granulation Process

Core particles were prepared from Composition I using a high speed mixer. The core particles were dried and classified. The core particles were rolled in a pan granulator, while spraying an aqueous solution of Composition II over the core particles. Thus, a granular quinine preparation coated with the lipid sample was prepared.

A control coated granular quinine preparation was also prepared in the same manner except that no lipid sample was incorporated and the amount of hydroxypropylcellulose was changed to 6 parts in Composition II. A comparative coated granular quinine preparation was further prepared in the same manner except that the lipid sample 1 was replaced with the same amount of lecithin (i.e., phosphatidylcholine).

The coated granular preparation sample was subjected to sensory evaluation by the equivalent concentration test. A panel of ten to fifteen members having normal sense of taste was employed. In the test, each member kept 0.5 g of the granular preparation sample in his mouth for 30 seconds and gave his evaluation.

The results are set forth in Table 10.

TABLE 10

| Coated Granular preparation of quinine hydrochloride | Bitterness Level(average) |
|---|---|
| Coated granular preparation(control) | 8.3 |
| Granular preparation coated with Lipid Sample 1 | 2.9 |
| Granular preparation coated with lecithin (comparative) | 7.5 |

It is apparent that the coating of Lipid Sample 1 according to the invention suppresses bitter taste of quinine hydrochloride. Accordingly, a coated granular quinine preparation which is easily administered orally can be prepared.

EXAMPLE 15

Test Sample: Quinine Hydrochloride

A coated granular preparation was prepared from the following compositions I and II by the rolling granulation process described in Example 14.

| Composition I | |
|---|---|
| Quinine hydrochloride (active component) | 10 parts |
| Corn starch | 27 parts |
| Lactose | 44.5 parts |
| Hydroxypropylcellulose(content: 15%) | 3.5 parts |
| Composition II | |
| Lipid sample 1 | 10 parts |
| Hydroxypropylcellulose(content: 15%) | 5 parts |

A control coated granular quinine preparation was also prepared in the same manner except that no lipid sample was incorporated and the amount of hydroxypropylcellulose was changed to 15 parts in Composition II. A comparative coated granular quinine preparation was further prepared in the same manner except that the lipid sample 1 was replaced with the same amount of lecithin (i.e., phosphatidylcholine).

The granular preparation sample was subjected to sensory evaluation by the equivalent concentration test in the same manner as in Example 14.

The results are set forth in Table 11.

TABLE 11

| Coated granular preparation quinine hydrochloride | Bitterness Level(average) |
|---|---|
| Coated granular preparation(control) | 9.7 |
| Granular preparation coated with Lipid Sample 1 | 4.6 |

TABLE 11-continued

| Coated granular preparation quinine hydrochloride | Bitterness Level(average) |
|---|---|
| Granular preparation coated with lecithin (comparative) | 9.2 |

It is apparent that the coating of Lipid Sample 1 according to the invention suppresses bitter taste of quinine hydrochloride. Accordingly, a coated granular quinine preparation which is easily administered orally can be prepared.

EXAMPLE 16

Test Samples: Promethazine, Papaverine, Chloropromazine, Propranolol, Berberine

A coated granular preparation was prepared in the same manner as in Example 15 except for replacing quinine hydrochloride with the above test sample.

As a result, suppression of a bitter taste of the test sample by the coated lipid sample was confirmed.

EXAMPLE 17

Test Sample: Coptidis Rhizoma Pulveratum

A granular chinese extract medicine containing 20% of the test sample was prepared by dry granulation process. The granular medicine was coated with a mixture of 5 parts of Lipid Sample 1 and 5 parts of hydroxypropylcellulose by the pan-coating method.

As a result, suppression of a bitter taste of the test sample by the coated lipid sample was also confirmed.

EXAMPLE 18

Test Sample: Quinine Hydrochloride

A coated pellet preparation was prepared from the following compositions I and II.

| Composition I | |
|---|---|
| Quinine hydrochloride (active component) | 1 part |
| Corn starch | 30 parts |
| Lactose | 55 parts |
| Talc | 1 part |
| Hydroxypropylcellulose(content: 15%) | 3 parts |
| Composition II | |
| Lipid sample 1 | 5 parts |
| Hydroxypropylcellulose(content: 15%) | 5 parts |

Preparation of Pellets

The powdery Composition I was pressed to give pellets (250 mg/pellet) using a pelleting machine. Over the obtained pellet was coated Composition II by pan-coating process to give a coated pellet.

A control coated quinine pellet was also prepared in the same manner except that no lipid sample was incorporated in Composition II.

The pellet sample was subjected to sensory evaluation by the same equivalent concentration test as that described in Example 14.

The results are set forth in Table 12.

TABLE 12

| Coated pallet of quinine hydrochloride | Bitterness Level(average) |
|---|---|
| Coated pellet(control) | 8.0 |
| Pellet coated with Lipid Sample 1 | 2.5 |

It is apparent that the coating of Lipid Sample 1 according to the invention suppresses bitter taste of quinine hydrochloride. Accordingly, a coated granular quinine preparation which is easily administered orally can be prepared.

EXAMPLE 19

Test Sample: Quinine Hydrochloride

A coated pellet preparation was prepared from the following compositions I and II by the same process as that described in Example 18.

| Composition I | |
|---|---|
| Quinine hydrochloride (active component) | 10 parts |
| Corn starch | 30 parts |
| Lactose | 46 parts |
| Talc | 1 part |
| Hydroxypropylcellulose(content: 15%) | 3 parts |
| Composition II | |
| Lipid sample 1 | 5 parts |
| Hydroxypropylcellulose(content: 15%) | 5 parts |

A control coated quinine pellet was also prepared in the same manner except that no lipid sample was incorporated in Composition II.

The pellet sample was subjected to sensory evaluation by the same equivalent concentration test as that described in Example 14.

The results are set forth in Table 13.

TABLE 13

| Coated pallet of quinine hydrochloride | Bitterness Level(average) |
|---|---|
| Coated pellet(control) | 9.0 |
| Pellet coated with Lipid Sample 1 | 3.5 |

It is apparent that the coating of Lipid Sample 1 according to the invention suppresses bitter taste of quinine hydrochloride. Accordingly, a coated granular quinine preparation which is easily administered orally can be prepared.

EXAMPLE 20

Test Samples: Promethazine, Papaverine, Chloropromazine, Propranolol, Berberine

A coated pellet preparation was prepared in the same manner as in Example 19 except for replacing quinine hydrochloride with the above test sample.

As a result, suppression of a bitter taste of the test sample by the coated lipid sample was confirmed.

EXAMPLE 21

Test Sample: Powdery Quinine Hydrochloride

One part of powder quinine hydrochloride was coated with a mixture of 1 part of Lipid Sample 1 and 1 part of hydroxypropylcellulose (content: 15%) by spraying method on a fluidized bed. Thus coated powdery quinine hydrochloride was processed to give a powdery preparation, granular preparation, and pellets. The powdery preparation was produced in a V-blender. The granular preparation was produced by granulation process on a fluidized bed. The pellets were produced by means of a pelleting machine.

The compositions (in terms of parts) of the powdery preparation, granular preparation, and pellets are set forth below.

| Composition | Powdery | Granular | Pellets |
|---|---|---|---|
| Coated quinine hydrochloride | 3 | 3 | 3 |
| Corn starch | 30 | 30 | 30 |
| Lactose | 67 | 64 | 63 |
| Talc | — | — | 1 |
| Hydroxypropylcellulose | — | 3 | 3 |

It was confirmed that almost no bitter taste was sensed on the powdery preparation, granular preparation, and pellets.

EXAMPLE 22

Test Sample: Quinine Hydrochloride 1 mM aqueous quinine hydrochloride solution was prepared and used as standard solution.

Using the standard solution, the following sample solutions were prepared:

Sample Solution I

In 100 parts of the standard solution was dispersed 0.3 part of phosphatidic acid.

Sample Solution II

In 100 parts of the standard solution were dispersed 0.3 part of phosphatidic acid and 0.7 part of ovalbumin.

Sample Solution III

In 100 parts of the standard solution was dispersed 0.3 part of soybean lecithin.

Sample Solution IV

In 100 parts of the standard solution were dispersed 0.3 part of rapeseed oil and $\beta$-lactoglobulin.

The sample solution was subjected to sensory evaluation by the equivalent concentration test. The results are set forth in Table 14.

TABLE 14

| Sample solution | Bitterness Level |
|---|---|
| Standard solution | 1.00 |
| Sample solution I | 0.113 ± 0.022 |
| Sample solution II | 0.097 ± 0.017 |
| Sample solution III | 0.994 ± 0.028 |
| Sample solution IV | 0.992 ± 0.085 |

It is apparent that the addition of phosphatidic acid according to the invention suppresses bitter taste of quinine hydrochloride.

EXAMPLE 23

Test Sample: Quinine Hydrochloride

In 100 mL of deionized water was dissolved 0.04 g of the powdery test sample. To the solution were added 3 g of phosphatidic acid and 3 g of lactose. The mixture was stirred and made homogenous in a homogenizer. The obtained emulsion was dehydrated in a freeze-dryer to give a powder containing quinine hydrochloride and phosphatidic acid. The produced powder gave almost no bitter taste.

EXAMPLE 24

Test Sample: Herring Roe

In an aqueous dispersion of Lipid Sample 1 (5%) was placed for 30 minutes herring roe free from salt. Thus, herring roe having the lipid sample on its surface. Thus treated herring roe gave delicious taste with reduced bitterness.

EXAMPLE 25

Test Sample: Bracken

A bracken (known as having a strong bitter taste) was treated for removal of harshness in a conventional manner and then placed in an aqueous dispersion of Lipid Sample 1 (10%) for 30 minutes. Thus treated bracken gave favorable taste with reduced bitterness.

EXAMPLE 26

Test Samples: Quinine Hydrochloride and Caffeine

In purified water was incorporated Lipid Sample 3 under stirring to give 3% aqueous dispersion.

The obtained aqueous dispersion was kept for about 10 min in the mouth of a member of panel. The member rinsed his mouth with the dispersion to spread it inside of the mouth and then to vomit the dispersion. Thereafter, he placed in his mouth an aqueous quinine hydrochloride solution (0.5 mM) or an aqueous caffeine solution (50 mM) to examine the bitter taste of the placed material.

The same test was repeated using water, an aqueous sucrose solution (10%), or an aqueous lecithin dispersion (3.0%) in place of the aqueous lipid sample solution.

The evaluation was made by the equivalent concentration test.

The results are set forth in Table 15.

TABLE 15

| | Bitterness Level(average) |
|---|---|
| For quinine hydrochloride | |
| Dispersion of Lipid Sample 3 | 5.9 |
| Water (control) | 9.2 |
| Sucrose solution (comparative) | 9.1 |
| Lecithin dispersion (comparative) | 8.8 |
| For caffeine | |
| Dispersion of Lipid Sample 3 | 5.5 |
| Water (control) | 9.0 |
| Sucrose solution (comparative) | 8.6 |
| Lecithin dispersion (comparative) | 8.1 |

It is understood that the pretreatment with Lipid Sample 2 according to the invention obviates sensing of bitter taste of material.

EXAMPLE 27

It is known that the taste organ of frog is similar to human being in sensing bitter tastes. Thus, examination of reduction of bitter tastes using the taste organ has been generally employed for evaluating reduction of bitter tastes for human being.

The test method is as follows.

A frog is anesthetized using urethane. The outer side of the mandible of the anesthetized frog is cut open to expose its hypopharynx nerve. Its central side is cut and brought into contact with a silver electrode. An electric signal (neuroimpulse) produced by stimulus of bitterness is multiplied and integrated to record using a pen recorder. In the test, the strength of bitter taste is understood to correspond to the height of response just after the stimulus takes place. The stimulus is applied to the tongue by flowing 10 mL of a sample solution at a flow rate of 1.5 mL/sec. Strychnine nitrate is used as a substance having a bitter taste. The examination is performed by the following sample solutions:

(1) aqueous strychnine nitrate solution (1 mM);

(2) aqueous strychnine nitrate solution (1 mM) in which 0.85 part of phosphatidic acid is dispersed per 100 parts of the solution;

(3) aqueous strychnine nitrate solution (1 mM) in which 0.85 part of phosphatidic acid and 2.15 parts of β-lactoglobulin (serving as dispersant) are dispersed per 100 parts of the solution;

(4) aqueous strychnine nitrate solution (1 mM) in which 0.85 part of lysophosphatidic acid is dispersed per 100 parts of the solution;

(5) aqueous strychnine nitrate solution (1 mM) in which 0.85 part of rapeseed oil and 2.15 parts of β-lactoglobulin are dispersed per 100 parts of the solution; and (6) aqueous strychnine nitrate solution (1 mM) in which 3.0 parts of soybean lecithin is dispersed per 100 parts of the solution.

The results are illustrated in FIG. 1. The sample solutions (2), (3) and (4) which contain the acidic phospholipid or lysophospholipid show remarkable suppression of the bitter taste, while the sample solutions (1), (5) and (6) show no suppression of the bitter taste.

We claim:

1. A method for suppressing a bitter taste of a material to be placed in the mouth or in contact with the mouth, which comprises adding a bitter taste suppressing effective mount of a composition selected from the group consisting of acidic phospholipids or acidic lysophospholipids to the material, wherein the neutral lipid content of the composition is not more than 30 wt. % and the neutral phospholipid content of the composition is not more than 50 wt. %.

2. A method for suppressing a bitter taste of a pharmaceutical to be administered orally which comprises contacting the tongue with a bitter taste suppressing effective amount of a composition selected from the group consisting of acidic phospholipids or acidic lysophospholipids wherein the neutral lipid content of the composition is not more than 30 wt. % and the neutral phospholipid content of the composition is not more than 50 wt. % prior to oral administration of the pharmaceutical.

3. The method of claim 2 wherein the acidic phospholipid or lysophospholipid is phosphatidic acid or lysophosphatidic acid, respectively.

4. The method as defined in claim 1, wherein the acidic phospholipid or lysophospholipid is added to the material in the form of a lipid mixture containing at least 60 wt. % of the acidic phospholipid or lysophospholipid therein.

5. The method as defined in claim 1, wherein the acidic phospholipid or lysophospholipid is added to the material in the form of a lipid mixture whose neutral lipid content is less than 20 wt. %.

6. The method as defined in claim 1, wherein both the acidic phospholipid and lysophospholipid are added to the material.

7. The method as defined in claim 1, wherein the acidic phospholipid or lysophospholipid is phosphatidic acid or lysophosphatidic acid, respectively.

8. The method as defined in claim 1, wherein the material is selected from the group consisting of foods, drinks, pharmaceuticals for oral administration, tooth paste, and mouthwash.

9. The method as defined in claim 1, wherein the acidic phospholipid or lysophospholipid is coated on the surface of the material.

10. The method as defined in claim 1, wherein the acidic phospholipid or lysophospholipid is added in an amount of 0.01 to 60 weight parts to one weight part of the material.

11. The method as defined in claim 1, wherein the acidic phospholipid or lysophospholipid is added in an amount of 0.05 to 30 weight parts to one weight part of the material.

* * * * *